United States Patent
Comeau

(10) Patent No.: US 11,543,372 B2
(45) Date of Patent: Jan. 3, 2023

(54) SEAL VALIDATION WITH CHEMICAL PRE-TREATMENT

(71) Applicant: Dril-Quip, Inc., Houston, TX (US)

(72) Inventor: Kyle A. Comeau, Kingwood, TX (US)

(73) Assignee: Dril-Quip, Inc., Houston, TX (US)

( * ) Notice: Subject to any disclaimer, the term of this patent is extended or adjusted under 35 U.S.C. 154(b) by 353 days.

(21) Appl. No.: 16/872,900

(22) Filed: May 12, 2020

(65) Prior Publication Data
US 2021/0356384 A1    Nov. 18, 2021

(51) Int. Cl.
*G01N 25/02* (2006.01)
*G01M 3/02* (2006.01)
*G01M 13/005* (2019.01)
*G01N 33/00* (2006.01)

(52) U.S. Cl.
CPC .............. *G01N 25/02* (2013.01); *G01M 3/02* (2013.01); *G01M 13/005* (2013.01); *G01N 2033/009* (2013.01)

(58) Field of Classification Search
CPC ...... G01N 25/00–02; G01N 2033/009; G01M 3/00–02; G01M 13/005
See application file for complete search history.

(56) References Cited

U.S. PATENT DOCUMENTS 9,581,523 B2 * 2/2017 Anderson .............. F16J 15/064
9,958,358 B2 * 5/2018 Roe ....................... G01M 15/05

FOREIGN PATENT DOCUMENTS

CN    108088786 A    5/2018

OTHER PUBLICATIONS

"Useful lifetime prediction of rubber component" Elsevier Engineering Failure Analysis, Woo et al., Jan. 25, 2011 (Year: 2011).*
"Predicting the Life of TPT Seals in severe Service Environments" Seventh International Conference on Thermoplastic Elastomer Markets & Products, Lyeden et al., Feb. 12, 1993 (Year: 1993).*
Richter, B. "Evaluation of stability tests for elastomeric materials and seals." International Polymer Science and Technology 41.5 (2014): 1-6.

(Continued)

*Primary Examiner* — Nguyen Q. Ha
(74) *Attorney, Agent, or Firm* — Baker Botts L.L.P.

(57) ABSTRACT

Methods for performing seal validation with a chemical pre-treatment are provided. One such method includes establishing an Arrhenius relationship between a material property response of a material exposed to a test fluid based on experimental results of testing a plurality of material samples made of the material across multiple temperatures. The method also includes determining, based on the Arrhenius relationship, a pre-treatment time and a pre-treatment temperature that approximates a seal end-of-life condition. The method further includes pre-treating a seal by exposing the seal to the test fluid at the determined pre-treatment temperature for the determined pre-treatment time, the seal having at least in part a same material composition as the plurality of material samples, and after pre-treating the seal, performing one or more validation tests on the pre-treated seal.

20 Claims, 4 Drawing Sheets

(56) References Cited

OTHER PUBLICATIONS

Gillen, Kenneth T., Mathew Celina, and Robert Bernstein. "Validation of improved methods for predicting long-term elastomeric seal lifetimes from compression stress—relaxation and oxygen consumption techniques." Polymer Degradation and Stability 82.1 (2003): 25-35.

Search Report issued in related Great Britain Patent Application No. GB2106638.6 dated Feb. 16, 2022, 1 page.

\* cited by examiner

SEAL VALIDATION WITH CHEMICAL PRE-TREATMENT

TECHNICAL FIELD

The present disclosure relates generally to validating seals for use in a predetermined application and, more particularly, to a method for performing seal validation with a chemical pre-treatment.

BACKGROUND

In order to find and produce new oil and gas reserves, exploration continues to lead to greater depths within the ocean. As a result, Christmas tree and wellhead equipment must operate at greater depths and therefore must be capable of withstanding greater external hydrostatic head pressures. In addition, downhole equipment lowered through the well is often exposed to various chemicals during well completion and production operations. As such, seals (e.g., non-metallic seals) designed for use within these types of equipment must be properly tested and validated prior to use in a particular environment (e.g., a subsea or subterranean environment). Several existing methods for validating seals for use in these extreme environments do not address the long-term behavior of the seals used in permanent installations. Although some standards for validating seals provide an accurate estimate of total seal life and long-term behavior, the testing procedures are time-consuming and expensive. It is now recognized that a need exists for a low-cost seal validation method for evaluating the end-of-life behavior of seals for use in equipment installations.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Figure 1:
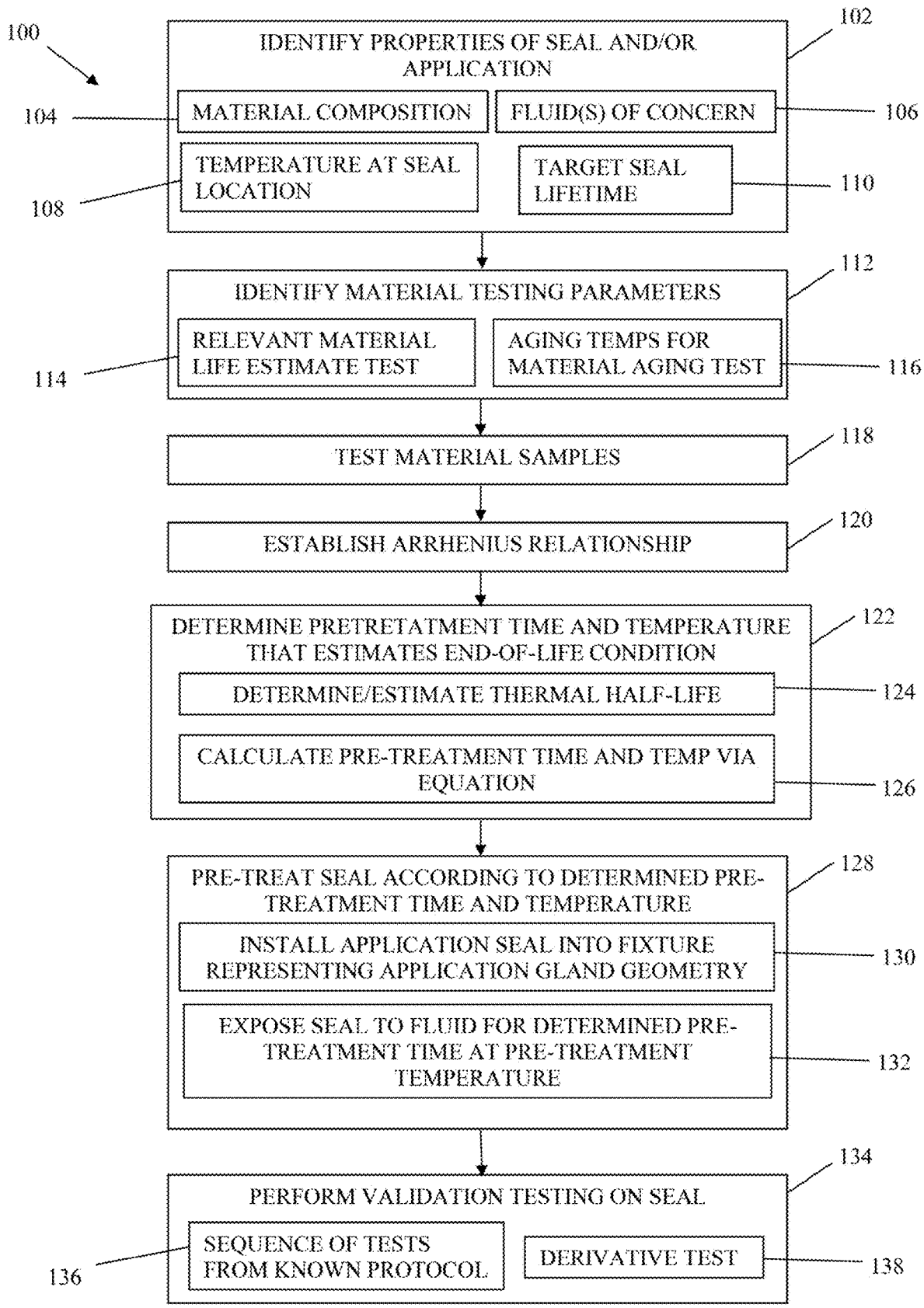
FIG. 1 is a process flow diagram illustrating a method for validating a seal for use in an equipment installation, in accordance with an embodiment of the present disclosure.

Illustrative embodiments of the present disclosure are described in detail herein. In the interest of clarity, not all features of an actual implementation are described in this specification. It will of course be appreciated that in the development of any such actual embodiment, numerous implementation specific decisions must be made to achieve developers' specific goals, such as compliance with system-related and business-related constraints, which will vary from one implementation to another. Moreover, it will be appreciated that such a development effort might be complex and time consuming but would nevertheless be a routine undertaking for those of ordinary skill in the art having the benefit of the present disclosure. Furthermore, in no way should the following examples be read to limit, or define, the scope of the disclosure.

Certain embodiments of the present disclosure may be directed to methods for validating a seal for use in an equipment installation. The disclosed methods may be particularly useful for validating a seal used in a subsea or subterranean installation. However, the disclosed methods may be used to validate a seal for use in any desired application requiring seal performance (or non-seal performance in applications like banding and lining) for a duration that is longer than is practical to test for. Similarly, the disclosed methods may be used to validate a seal for use in any desired application that uses fluids that are difficult to test at high pressures (like $H_2S$). The disclosed methods may present a user with seal performance results at an end-of-life condition of the seal. The methods involve testing simple material samples to develop a material response curve for a given chemical exposure and then using this curve to pre-treat an actual seal to the end-of-life state before performing validation testing.

The methods generally involve determining a pre-treatment to be performed on a new seal to approximate or replicate an end-of-life condition of the seal, pre-treating the seal according to the determined pre-treatment, and performing one or more validation tests on the pre-treated seal. Pre-treating the seal involves exposing the seal to a chemical environment for a predetermined length of time and at a predetermined temperature. The method may include testing a plurality of material samples having the same material composition of the seal to be validated and determining an Arrhenius relationship between a material property of the material samples and temperature. The method may then include determining the length of time and temperature for the pre-treatment of the seal based on the Arrhenius relationship of the material samples. The disclosed methods assume degradation of the material used to form the seal is related to degradation of the seal.

Since the methods include pre-treating the seal prior to performing validation testing on the seal, the validation testing provides a seal performance evaluation while considering material degradation at the end-of-life condition of the seal. This evaluation offers more valuable information than typical, inexpensive seal validation techniques, while costing far less and taking less time than a full investigation of the seal in accordance with, for example, the API TR 6JI elastomer life estimation testing procedures.

Turning now to the drawings, FIG. 1 is a process flow diagram of a method 100 for performing a seal validation with chemical pre-treatment, in accordance with an embodiment of the present disclosure. This method 100 may provide an enhanced validation process for a seal to be used in a particular environment (e.g. a subterranean or subsea environment). The validation process may provide information regarding the behavior of the seal at its end-of-life condition for a particular application without requiring large amounts of time (years of testing) or expense to perform the testing.

The method 100 of FIG. 1 is exemplary, and it should be understood that one or more steps of the illustrated method 100 may be performed in a different order, or eliminated, in other embodiments. In still other embodiments, the method 100 for performing seal validation with a chemical pretreatment may also include additional steps not shown in the illustrated embodiment, without departing from the scope of this disclosure.

In some embodiments, one or more portions of the methods of the present disclosure may be at least partially automated in that they may be performed by a computerized and/or robotic system without human intervention. In some embodiments, one or more components of the systems of the present disclosure may be designed to interface with one or more computer systems whereby data from the various tests and analytical methods described herein may be transmitted to the computer system electronically for display, storage, and/or further analysis.

The method 100 may include identifying (block 102) properties of the seal and/or properties of the application for which the seal is to be used. The seal may be constructed for use within a particular piece of equipment to be used in a predetermined environment (e.g., a subsea or subterranean environment). The application for which the seal is to be used may include specific operations performed by the piece of equipment and/or properties of the environment to which the equipment and seal will be exposed during these operations.

The seal may include a non-metallic seal (e.g., elastomeric seal) or a seal having at least one non-metallic portion. In some embodiments, the seal may take the form of an elastomeric seal having an o-ring or other construction used to provide a fluid tight seal between two pieces of equipment. In other embodiments, the seal may take the form of a metallic/non-metallic hybrid seal, such as a metal end cap seal designed to be deformed and locked in place between two pieces of equipment (e.g., in a subsea wellhead). Properties of the seal may include, for example, the material composition of the seal (block 104), including any sensitive material(s) from which the seal is constructed. In some embodiments, properties of the seal may also include the shape, size, or construction of the seal.

Properties of the application in which the seal is designed to be used may include, for example, one or more fluids of concern (block 106), an expected temperature at the seal location (block 108), a target seal lifetime (block 110), and the like. The one or more fluids of concern (block 106) may be fluids to which the seal material (block 104) is known to be sensitive, generally corrosive fluids to which the seal will be exposed during a subsea or subterranean operation, or a sequence of fluids that the seal would be exposed to over time during operations performed in a subsea or subterranean environment. The expected temperature at the seal location (block 108) may be predetermined based on sensor measurements taken during similar downhole/subsea operations, modeling of an ambient temperature of a subterranean environment made during exploration, and the like. The expected temperature (block 108) may include an expected average temperature at the seal location or an expected maximum temperature at the seal location, given the operations being performed. The target seal lifetime (block 110) is a length of time that the seal is expected to perform its sealing function within the equipment in which it is installed. The target seal lifetime (block 110) may be a length of time in which the equipment is expected to be deployed and/or used in the application environment.

The method 100 may then include identifying (block 112) material testing parameters for testing material samples to develop an Arrhenius response curve for the material that will be used to construct the seal. The material testing parameters may include, for example, a relevant material life estimation test (block 114) for the material from which the seal will be constructed. The relevant material life estimation test (block 114) may be determined based on the identified seal/application parameters (block 102) for the seal. The material life estimation test (block 114) may be any desired material property tests that can be performed on a material sample such as, for example, tensile or compression tests, torsion tests, bending tests, impact tests, corrosion tests, chemical analysis techniques (e.g., Fourier-transform infrared spectroscopy (FTIR)), thermal property modeling (e.g., differential scanning calorimetry (DSC), thermomechanical analysis (TMA)), and so forth. The material life estimation test (block 114) may be selected to provide information on the most critical material property (e.g., most likely failure mode) for the specific seal/application, based on the known properties of the seal material, the shape and construction of the seal, the properties of the fluid to which the seal will be exposed, and the operation being performed by the seal.

The material testing parameters may also include, for example, at least two aging temperatures (block 116) at which the material samples will be aged prior to performing the selected material life estimation test (block 114). The aging temperatures (block 116) may be selected at least partially based on the expected temperature (block 108) for the application of the seal.

The testing parameters may be identified (block 112) from an available list of tests or a battery of tests typically performed on material samples under existing seal validation protocols. As an example, the material life estimation test (block 114) and aging temperatures (block 116) may be selected from a list of relevant tests and aging temperatures outlined in the protocol for one or more existing seal testing standards. These seal testing standards may include, for example, those described in the NORSOK M-710 (Rev. 2) Qualification of non-metallic sealing materials and manufactures, the NORSOK M-710 (Ed. 3) Qualification of non-metallic materials and manufacturers—Polymers, or the ISO 23936-2 Petroleum, petrochemical and natural gas industries—non-metallic materials in contact with media related to oil and gas production standard. Other available testing standards may be used in the selection of a desired material life estimation test (block 114) and aging temperatures (block 116) for a particular seal material and application.

Once the testing parameters are identified, the method 100 may include testing (block 118) material samples according to the identified material life estimation test after aging the material samples at the identified aging temperatures. The material samples may be exposed to a test fluid (i.e., the determined fluid of concern) during the aging portion of the testing (block 118). The test fluid has the same fluid composition of the fluid(s) expected to be encountered in the seal application. The testing (block 118) may involve exposing a plurality of material samples to the test fluid while holding the material samples and fluid at a first aging temperature. At different aging times, the material samples may be removed from the aging environment and the material properties of the samples tested. The same process is repeated with material samples that are aged at the second aging temperature. That is, a plurality of material samples may be exposed to the test fluid while being held at the second aging temperature, and then at different aging times the material samples are removed from the aging environment and tested.

In other embodiments, the testing (block 118) may involve exposing all of the material samples to the test fluid while holding the material samples and fluid at a first aging temperature only. In such embodiments, the plurality of material samples may be tested after being exposed to the test fluid at the first aging temperature for different lengths of aging time. Then, an estimate of an Arrhenius curve may be calculated. The Arrhenius curve may be estimated as having a slope that what would yield a conservative thermal half-life for the material property being investigated. The "thermal half-life" described in this application is a negative number representing a difference between two temperature values provided in absolute temperature units (e.g., in Kelvin or Rankine). If temperature measurements are provided in Kelvin during testing, a conservative thermal half-life may be between −5 and −15, or more particularly −10. If temperature measurements are provided in Rankine during testing, a conservative thermal half-life may be between −9 and −27, or more particularly −18. Details on determining a thermal half-life of the material property are provided below.

The method 100 includes establishing an Arrhenius response (block 120) of the material in the specified chemical environment based on the results of the testing (block 118). The Arrhenius response (block 120) of the material may be experimentally determined. For example, the Arrhenius response (block 120) may be determined via one of the above listed existing testing methodologies (e.g., NORSOK M-710 or ISO 23936-2). The Arrhenius response (block 120) is a relationship between a time to failure (TtF) of the material sample and a temperature (T) at which the material sample was aged in the test fluid. More specifically, the Arrhenius response (block 120) may be a linear relationship between the natural logarithm (ln) of TtF and 1/T, as in the following equation.

$$\frac{1}{T} = \ln(TtF)x + y \qquad (1)$$

Upon establishing the Arrhenius response (block 120) of the material by testing the material samples, the method 100 includes determining (block 122) a pre-treatment time and a pre-treatment temperature that estimates an end-of-life condition of the seal exposed to the expected temperature (block 108) of the seal application for the target seal lifetime (block 110). In the equations discussed below, the expected temperature (block 108) of the seal application is referred to as $T_{App}$, the target seal lifetime (block 110) is referred to as $t_{App}$, the pre-treatment temperature is referred to as $T_{PT}$, and the pre-treatment time is referred to as $t_{PT}$.

Determining (block 122) the pre-treatment time and temperature based on the Arrhenius relationship may include first determining or estimating a thermal half-life (block 124) of the material property that deteriorates fastest, or the most critical material property (i.e., most likely failure mode) based on the Arrhenius relationship and known application and/or seal testing parameters. Determining the thermal half-life (block 124) may include using the experimentally determined Arrhenius curve (linear) and picking a first point on the curve representing $(1/T_1, \ln(t_1))$, where $T_1$ represents the absolute temperature and $t_1$ represents the time to failure (TtF) at that temperature $T_1$. The thermal half-life determination (block 124) may then include finding or calculating a second point $(1/T_2, \ln(t_2))$ on the Arrhenius curve, where $$t_1 = 2 \times t_2 \qquad (2)$$

The thermal half-life (h) is then estimated according to the equation:

$$h = T_1 - T_2 \qquad (3)$$

In some embodiments, determining the thermal half-life (block 124) of the material property may involve determining an effective thermal half-life, as described in detail below. In other embodiments, a thermal half-life (block 124) may be estimated to be a conservative value, for example, between −5 and −15, or more particularly −10. Upon determining or estimating the thermal half-life (block 124), the pre-treatment time ($t_{PT}$) and/or pre-treatment temperature ($T_{PT}$) are calculated (block 126) based on the following equation.

$$t_{PT} = t_{App} \times 2^{\wedge\left(\frac{T_{PT} - T_{App}}{h}\right)} \qquad (4)$$

Since $T_{App}$ and $t_{App}$ are known (e.g., from block 104), both $T_{PT}$ and $t_{PT}$ may be determined using this equation and the experimentally determined Arrhenius relationship. In some embodiments, one of the values $t_{TP}$ or $T_{TP}$ may be pre-selected based on constraints for the testing and validation process. For example, the value of tip may be chosen to be the longest tolerable amount of time for the pre-treatment. This allows the lowest $T_{PT}$ value to be used for a longer time, thereby maximizing relevance of the pre-treatment to actual seal end-of-life conditions.

The calculated thermal half-life (h) will vary based on the value of $t_1$ and $t_2$ that are used for the above calculations. For a better approximation of the pre-treatment variables, an effective thermal half-life ($h_{eff}$) may be calculated and used as the h in Equation 4 above. The effective thermal half-life ($h_{eff}$) may be equal to the average of two calculated half-lives determined using both $t_{PT}$ and $t_{App}$ as values of $t_1$. In some embodiments, it is desirable to use $t_{PT}$ as the lower $t_1$ value if $t_{PT}$ is already known, and to use $t_{App}$ as the higher $t_1$ value. In other embodiments, if the value of $t_{PT}$ is not known, an estimate of $t_{PT}$ may be used as the lower $t_1$ value while $t_{App}$ is used as the higher $t_1$ value. For a relatively conservative thermal half-life determination, the calculated thermal half-life ($h_{eff}$) may be the larger thermal half-life determined for $t_1 = t_{PT}$.

As mentioned above, in some embodiments the Arrhenius relationship (block 120) may be estimated based on measurements that form just one point (as opposed to two or more) on the Arrhenius curve. The slope of the Arrhenius curve may be estimated using an assumption of a conservative thermal half-life for Kelvin temperature measurements (e.g., between −5 and −15, or more particularly −10). To determine the slope, values for $t_1$ and $T_1$ may be taken from the one known point on the Arrhenius curve. With the example assumption that h=−10 (for absolute temperatures in Kelvin), the estimated value of $T_2$ is $T_1 + 10$, and the value of $t_2$ is $t_1/2$. The resulting determination of $T_2$ and $t_2$ may then be used to plot a second point $(1/T_2, \ln(t_2))$ of the Arrhenius curve, and the Arrhenius response calculated from points $(1/T_1, \ln(t_1))$ and $(1/T_2, \ln(t_2))$. This may cut down on the length of time involved in performing the material sample testing and, thus, the overall method, at the sacrifice of accuracy.

After determining the pre-treatment (block 122) for the seal based on the Arrhenius response curve of the tested material samples, the method 100 includes performing a pre-treatment (block 128) of a seal made at least in part from the same material composition as the material samples. In some embodiments, the seal may be entirely constructed from a material having the same material composition as the material samples. In other embodiments, the seal may be constructed partially from a material having the same material composition as the material samples and partially from one or more other materials. As an example, the seal may include an S-seal made primarily from an elastomer and containing metal springs as anti-extrusion mechanisms. In such embodiments, the bulk elastomer has the same material composition as the material samples that were tested, as the bulk elastomer has the greatest susceptibility to degradation. As another example, the seal may include a pressure inverting pedestal (PIP) seal that contains multiple materials such as, for example, a hard elastomer "jacket," a soft elastomer "o-spring," and a hard thermoplastic energizing "PIP ring." In such embodiments, one or both of the elastomers may have the same material composition as material samples that were tested, since the elastomers are expected to degrade faster than the thermoplastic of the PIP ring. If both elastomer materials are tested, then an Arrhenius curve may be determined (or estimated) for each elastomer, and the pre-treatment that will yield an end-of-life condition for one of the two elastomers first may be performed. This pre-treatment will be performed on the entire seal, including all three materials.

The pre-treatment is performed according to the determined pre-treatment time ($t_{PT}$) and temperature ($T_{PT}$) described above. Pre-treating (block 128) the seal may include installing (block 130) a new seal in a representative gland and exposing (block 132) the seal to the application fluid, which is the same as the test fluid used in the earlier testing (block 118). The representative gland may have exactly the same geometry or approximately the same geometry as the equipment in which an actual seal will be used for the predetermined application. The seal is exposed to the application fluid at the determined pre-treatment temperature ($T_{PT}$) for the determined length of pre-treatment time ($t_{PT}$). Pre-treating the seal (block 128) according to the determined pre-treatment variables approximates the wear that would otherwise occur in the seal over its expected lifetime ($t_{App}$) when kept at the application temperature ($T_{App}$). It should be noted that the pre-treatment (block 128) relies on an assumption that the Arrhenius relationship (block 120) determined for arbitrary material property changes is the same as when dealing with seal changes.

After pre-treating the seal (block 128), the method includes performing additional validation testing (block 134) of the pre-treated seal. This validation testing (block 134) may include one or more customized tests to estimate how a seal used in the predetermined (e.g., subsea or subterranean) environment will perform at the end of its life. The validation testing (block 134) may be performed on the pre-treated seal immediately after the pre-treatment is completed. The validation testing (block 134) may include a number of tests that would typically be performed using a "new" seal. In some embodiments, for example, the validation testing (block 134) may include a sequence of tests used in a known seal validation protocol (block 136). This sequence of tests (block 136) may be performed on the seal as the seal is placed in a test fixture and subjected to changes in temperature and pressure in a prescribed sequence. In some instances, the pre-treated seal may not be cold-tested as would normally be done for a "new" seal, since it may be difficult to cold test the pre-treated seal if it has been pre-treated in a fluid that can freeze at the cold test temperature.

In other embodiments, the validation testing (block 134) may involve performing a derivative test (block 138) to simulate a seal response to an environmental change. The environmental change being simulated may include, for example, an upstream leak that occurs toward the end-of-life of the seal, suddenly causing the aged seal to experience additional pressure and a different chemical environment. In such an instance, the seal may be pre-treated (block 128) in a first chemical environment (same fluid as the test fluid, at a first application pressure), and then the seal is exposed (block 138) for an extended period of time to another, different chemical environment (having a different fluid composition than the test fluid, and at a pressure higher than the first application pressure).

Upon subjecting the seal to the desired validation testing (block 134), the seal may be removed from the test fixture and visually inspected to determine the wear and results of the validation testing. Since the seal was pre-treated to near an end-of-life condition before the validation testing (block 134), the results of the validation test will provide information about the end-of-life behavior of a seal made from the selected material. This provides more detailed information than would be available through the initial material testing (block 118) alone, but without the added cost and time associated with performing a full seal life estimation test under, for example, an API TR 6J1 seal life estimation testing procedure. As such, the disclosed seal validation method 100 provides a relatively low cost and less time-consuming process for obtaining information regarding end-of-life behavior of a seal for use in predetermined application.

Having described the disclosed method 100 for seal validation, a detailed example of this validation process will now be provided with reference to FIGS. 2A-6. In this example, the identified seal/application properties (e.g., block 102 of FIG. 1) may be as follows. The seal material in the example is unspecified and is therefore referred to as "Material XYZ." The test fluid to which the material samples and seal will be exposed is unspecified as well. However, the fluid is representative of a fluid/chemical to which an equivalent seal is expected to be exposed during a subsea or subterranean application in which the seal will be used. The temperature at the seal location within the subsea or subterranean equipment is expected to be 120° C. The target lifetime for the seal in this location is 20 years. These factors of the seal and its application environment may be identified (e.g., block 102 of FIG. 1) or estimated based on information regarding the subsea or subterranean application and material properties of the seal to be validated.

In this example, the identified material testing parameters (e.g., block 104 of FIG. 1) are as follows. The material property that is most relevant to seal life estimation is elongation at break (i.e., tensile strain). The aging temperatures for the material aging tests are 135° C. and 150° C. These material testing parameters may be identified based on material properties of the seal to be validated and using recommendations from existing test standards such as, for example, the NORSOK M-710 Qualification of non-metallic sealing materials and manufactures.

Figure 2A:
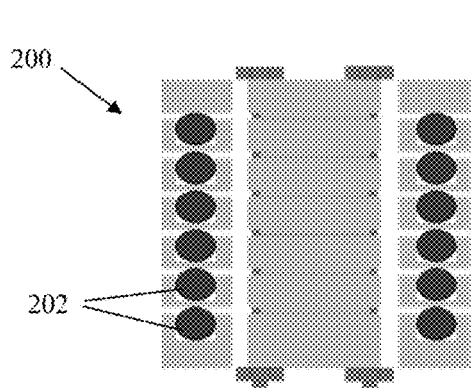
FIGS. 2A and 2B are schematic cross-sectional and top views of a fixture for aging material samples, in accordance with an embodiment of the present disclosure.
Figure 2B:
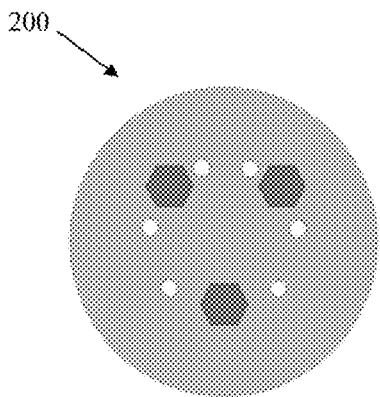

As discussed above with reference to FIG. 1, the relevant material property is tested for a number of material samples each exposed to the test fluid at one of the aging temperatures. FIGS. 2A and 2B illustrate an embodiment of a test fixture 200 in which material samples 202 may be aged in contact with a test fluid. As illustrated, the test fixture 200 may hold a number of material samples 202 in contact with the test fluid and at a desired temperature. Testing the material samples 202 (e.g., block 118 of FIG. 1) may involve aging the material samples 202 in the test fixture 200 for a certain length of time, removing the material samples 202 from the test fixture 200, and performing a tensile test on each material sample 202 to failure. During the tensile test, strain is recorded so that a determination of the elongation at break can be made for each material sample 202. The test fixture 200 may be maintained at a desired aging temperature for the entire length of time during which the material samples 202 are aged in the test fixture 200.

Material samples 202 aged in a test fixture(s) 200 may be mechanically tested after different lengths of aging time within the test fluid. For example, one or more material samples 202 may be tested after being exposed to the test fluid for 45 days, one or more material samples 202 may be tested after being exposed to the test fluid for 90 days, one or more material samples 202 may be tested after being exposed to the test fluid for 180 days, and one or more material samples 202 may be tested after being exposed to the test fluid for 365 days. In some embodiments, all material samples 202 within a given test fixture 200 may be tested after the same length of aging time. In other embodiments, different material samples 202 within the same test fixture 200 may be removed from the fixture 200 at different times for tensile testing.

This process of aging and tensile testing material samples 202 is performed at least twice at different temperatures, using the same material and test fluid combination. The test results for material samples 202 tested at different temperatures may be used to determine the Arrhenius relationship (e.g., block 120 of FIG. 1) of the material, as described below.

Figure 3:
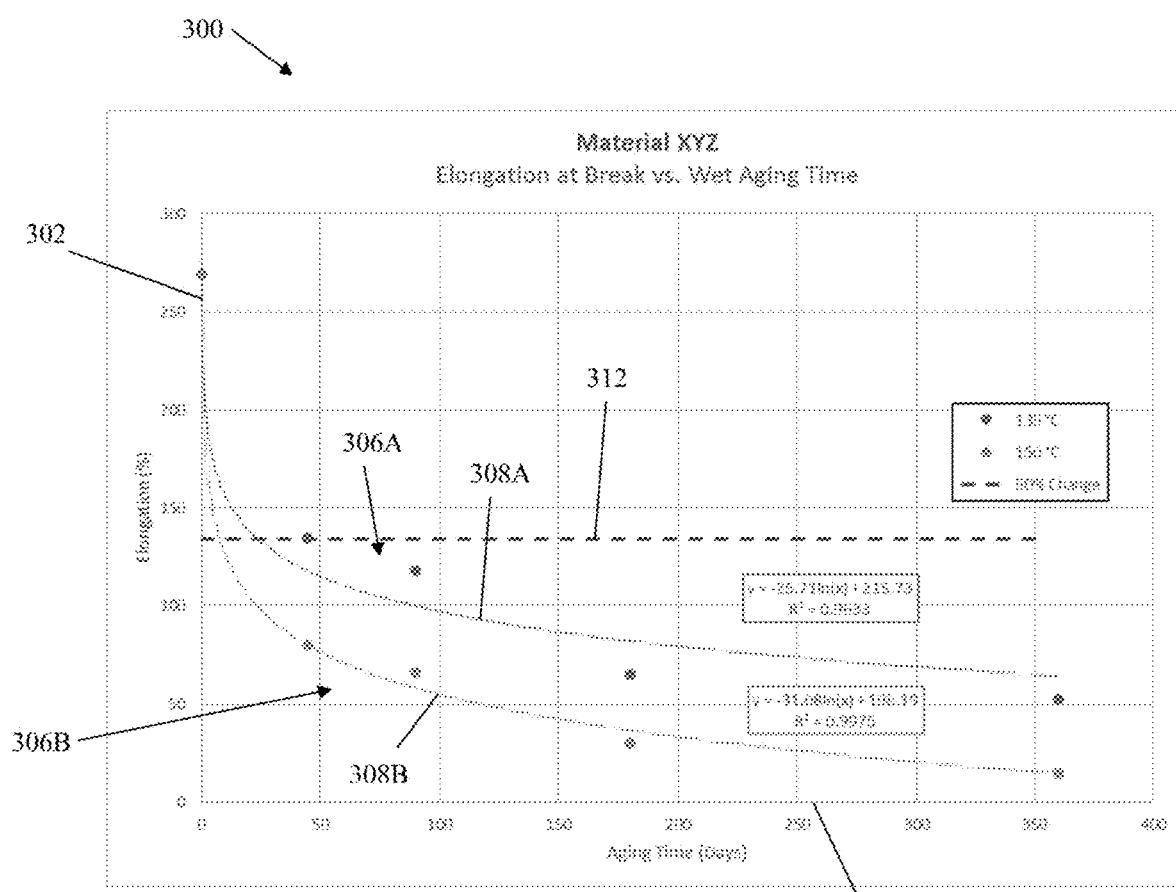
FIG. 3 is a plot representing a material response vs. aging time for material samples of the same material being tested at different temperatures, in accordance with an embodiment of the present disclosure.

Upon removing the material samples 202 from the test fixture(s) 200 and performing tensile tests after the desired aging times, results of the tensile tests for material samples 202 aged at different temperatures may be recorded. FIG. 3 is a plot 300 illustrating the results of tensile tests performed on the material samples (e.g., 202 of FIG. 2) after aging in the test fluid for different aging times (i.e., 45, 90, 180, and 365 days). The plot 300 shows the measured elongation at break 302 with respect to aging time 304. The plot 300 includes two datasets 306A and 306B, one (306A) for material samples aged at a first temperature (135° C.) and the other (306B) for material samples aged at a second temperature (150° C.). In each dataset, one or more material samples 202 were tested until failure after the desired aging time. The average value for the elongation at break 302 for each aging time in a given dataset is plotted, as shown. The first dataset 306A is fit to a logarithmic curve 308A representing the material life test result (i.e., change in elongation) with respect aging time for the material samples aged in the test fluid at the first temperature (i.e., 135° C.). Similarly, the second dataset 306B is fit to a logarithmic curve 308B representing the material life test result (i.e., change in elongation) with respect to aging time for the material samples aged in the test fluid at the second temperature (i.e., 150° C.). As discussed above, different material life tests and/or different first and second temperatures than those used in the present example may be chosen for testing material samples to estimate the life of seals used in other applications. In addition, different fit models than the one described (i.e., logarithmic curve) may be used to determine how the material is behaving based on the experimental results. Any desired fit model may be applied as long as the resulting curve fits the experimental results.

Figure 4:
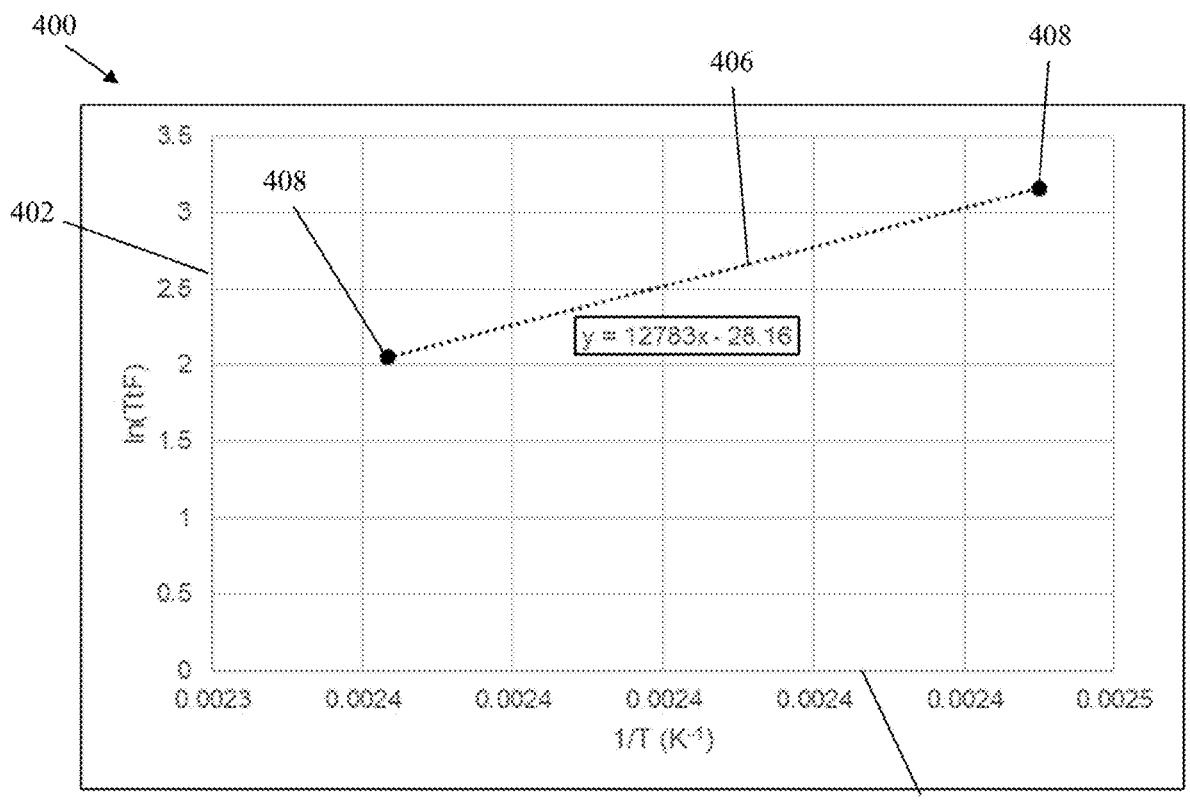
FIG. 4 is a plot representing an Arrhenius relationship between time to failure and temperature for a material determined based on the curves of FIG. 3, in accordance with an embodiment of the present disclosure.

The method then includes determining the Arrhenius relationship (e.g., block 120 of FIG. 1) between the results of the material life tests (e.g., block 118 of FIG. 1) described above and aging temperature. FIG. 4 is a plot 400 illustrating the Arrhenius relationship determined based on the previously obtained material life test results of FIG. 3. The plot 400 shows ln(TtF) 402 with respect to 1/T 404. TtF is a calculated "Time to Failure" of a material sample 202 aged at a particular temperature, and T is the aging temperature in Kelvins. In the example, the "Time to Failure" is determined to be equivalent to the time at which a material sample 202 aged at a particular temperature reaches a 50% change in elongation at break based on the tensile test results. The plot 300 in FIG. 3 includes a dashed line 312 representative of this 50% change in elongation. The TtF of the material sample aged at the first temperature (e.g., 135° C.) is determined to be the aging time at which the curve 308A fit to the first dataset 306A reaches the 50% change in elongation. Similarly, the TtF of the material sample aged at the second temperature (e.g., 150° C.) is determined to be the aging time at which the curve 308B fit to the second dataset 306B reaches the 50% change in elongation. As shown in FIG. 4, a linear curve 406 is fitted to two or more points 408 of ln(TtF) 402 versus 1/T 404 based on the results of the material tests. This linear curve 406 represents the determined Arrhenius relationship for a particular material aged in a particular fluid. In this example, the determined Arrhenius relationship for the material aged in the fluid is:

$$\ln(t) = 12783 \times \left(\frac{1}{T}\right) - 28.16 \tag{5}$$

After determining this Arrhenius relationship, the method includes determining (block 122 of FIG. 1) an acceptable pre-treatment time and temperature for pre-treating a seal in the fluid to approximate an end-of-life condition of the seal. The seal will be made from the same material as the material samples that were tested to determine the Arrhenius relationship. The determined pre-treatment time and pre-treatment temperature may represent the same end-of-life condition that would be reached if the seal were aged in the fluid for its entire target life at the application temperature. As discussed above, the target life and application temperature for the seal may have been previously identified (block 102 of FIG. 1). In this example, the target life of the seal is 20 years, and the application temperature is 120° C.

The acceptable pre-treatment time and pre-treatment temperature for aging the material to estimate the end-of-life condition may be bounded, for example, by a total length of time available (or desired) for performing the pre-treatment. In this example, there are only 30 days available to pre-treat the seal. As such, the pre-treatment time is determined to be 30 days. The pre-treatment temperature is determined to be the temperature at which treating the seal for 30 days will simulate 20 years of seal life at 120° C., based on the Arrhenius relationship. The following equations provide the determination of the pre-treatment temperature based on the Arrhenius relationship for the seal in this example.

First, the effective thermal half-life of the critical material property (e.g., tensile strain) is determined. This may involve calculating the thermal half-life of the critical material property using a $t_1$ value of the pre-treatment time, calculating the thermal half-life of the critical material property using a $t_1$ value of the application time, and calculating an average of the two half-lives. In this example, calculating the first thermal half-life involves determining the value of $T_1$, which is the temperature corresponding to the time to failure (TtF) for $t_1=30$ days based on the Arrhenius relationship, then determining the value of $T_2$, which is the temperature corresponding to the time to failure (TtF) for $t_2=15$ days (half of $t_1$).

$$t_1 = 30;$$

$$t_2 = \frac{1}{2} \times 30 = 15;$$

$$T_1 = \frac{12783}{\ln(30) + 28.16} \approx 405.02;$$

and $$T_2 = \frac{12783}{\ln(15) + 28.16} \approx 414.12.$$

The thermal half-life h of the critical material property at $t_1=30$ days is then determined as the difference between $T_1$ and $T_2$.

$$h = T_1 - T_2 \approx -9.1 \tag{6}$$

This process of determining the thermal half-life h is then repeated with $t_1$ being the application time. In this example, calculating this second thermal half-life involves determining the value of $T_1$, which is the temperature corresponding to the time to failure (TtF) for $t_1=7300$ days (20 years) based on the Arrhenius relationship, then determining the value of $T_2$, which is the temperature corresponding to the time to failure (TtF) for $t_2=3650$ days (half of $t_1$).

$$t_1 = 20 \times 365 = 7300;$$

$$t_2 = \frac{1}{2} \times 7300 = 3650;$$

$$T_1 = \frac{12783}{\ln(7300) + 28.16} \approx 344.97;$$

and $$T_2 = \frac{12783}{\ln(3650) + 28.16} \approx 351.54.$$

The thermal half-life h of the critical material property at $t_1=7300$ days is then determined as the difference between $T_1$ and $T_2$.

$$h = T_1 - T_2 \approx -6.6 \tag{7}$$

The effective thermal half-life is calculated by taking the average of the two determined half-lives.

$$h_{eff} = \frac{(-9.1) + (-6.6)}{2} = -7.85 \tag{8}$$

Then, the following equation can be used to calculate the pre-treatment temperature ($T_{PT}$).

$$t_{PT} = t_{App} \times 2^{\frac{(T_{PT} - T_{App})}{h_{eff}}} \tag{9}$$

In this example, the pre-treatment time $t_{PT}$ is 30 days, the application time $t_{App}$ is 20 years times 365 days, and the application temperature is 120° C. The results are as follows.

$$30 = (20 \times 365) \times 2^{\left(\frac{T_{PT} - 120}{-7.85}\right)} \tag{10}$$

$$T_{PT} = \frac{\ln\left(\frac{30}{20 \times 365}\right)}{\ln(2)} \times -7.85 + 120 \approx 182° \text{ C}.$$

This calculated pre-treatment temperature $T_{PT}$ is the temperature for a pre-treatment of the seal. Treating the seal at the calculated 182° C. for 30 days approximates the degradation of a seal aged at 120° C. for 20 years.

Figure 5:
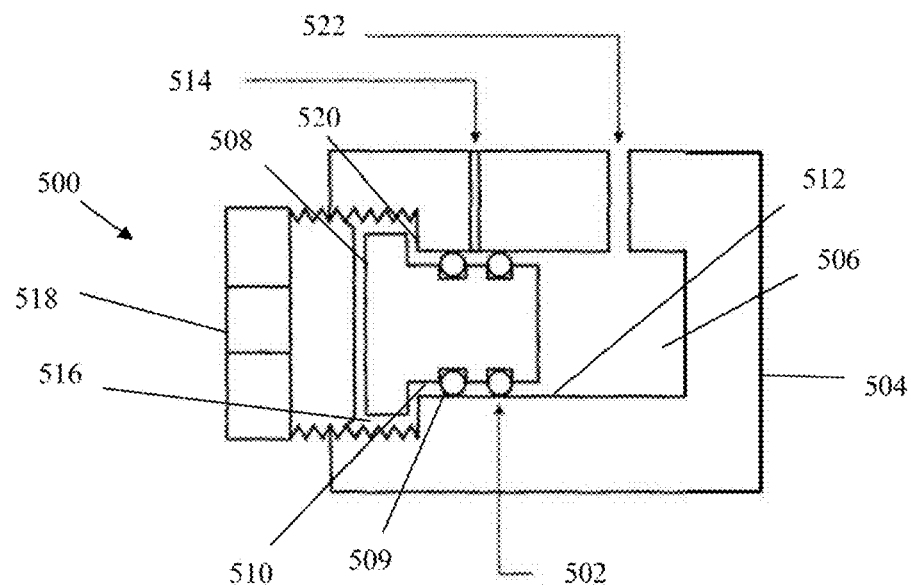
FIG. 5 is a schematic cross-sectional view of a pre-treatment fixture for a seal, in accordance with an embodiment of the present disclosure.

Upon determining this pre-treatment temperature, one or more seals having the same material composition of the material samples (e.g., 202 of FIG. 2) are pre-treated (block 128 of FIG. 1) for the pre-treatment time at the determined pre-treatment temperature. FIG. 5 illustrates a test assembly 500 into which a seal 502 may be loaded for performing the determined pre-treatment. At least a part of the seal 502 has the same material composition of the material samples that were previously tested to determine the Arrhenius relationship. In the illustrated embodiment, the test assembly 500 includes a housing 504 defining a chamber 506 into which a test fixture 508 is loaded. The seal 502 (e.g., an O-ring in FIG. 5) is disposed around the test fixture 508, along with another seal 509. The seal 509 may be made from a different material and have a different geometry from the seal 502 being tested. The assembly 500 is sized such that the seals 502 and 509 provide a fluid tight seal between an external surface 510 of the test fixture 508 and an internal wall 512 of the housing 504 defining the chamber 506. A leak detection port 514 extends through the housing 504 and is fluidly coupled to a space between the two seals 502 and 509 in the test fixture 508. A test fluid port 522 extends through the housing 504 and is used to provide pressurized fluid to an end of the chamber 506 that is sealed off by the seal 502. This end of the chamber 506 provides a pressurized service environment. The pressurized fluid provided through the test fluid port 522 has the same composition of the fluid used to age the material samples for generating the Arrhenius relationship.

The assembly 500 may be utilized to perform the pre-treatment of the seal 502 and to test operation of the seal 502 within the representative gland. The seal 502 is exposed to pressurized fluid provided through the test fluid port 522, and the leak detection port 514 may be monitored to confirm that the seal 502 is providing a fluidic seal within the assembly 500 during this pre-treatment.

The fixture 508 with the seals 502 and 509 may be loaded into the test assembly 500 through an opening 516 in a side of the housing 504. The fixture 508 may be secured in place within the housing 504 via a cap 518 inserted into and attached to the opening 516. Specifically, the cap 518 presses against the fixture 508 and holds the fixture 508 in place against an internal shoulder 520 of the housing 504. The housing 504 and test fixture 508 may be similar to, or adapted from, a test assembly used to provide seal testing under existing seal test protocols such as, for example, API Spec 6A: Specification for Wellhead and Christmas Tree Equipment, Section F.1.11 (pressure and temperature cycles).

The test assembly 500 and/or fluid communicated therethrough may be heated to the pre-treatment temperature (e.g., 182° C.) and held at this temperature for the entire pre-treatment time period (e.g., 30 days). During the pre-treatment time period, the seals 502 may be exposed to the pressurized pre-treatment fluid. This helps to speedily degrade the seals 502 to approximately an end-of-life condition. The pre-treatment performed via the test assembly 500 may degrade the seals 502 to approximately the same end-of-life condition that would be encountered if the seals 502 were exposed to the same fluid for 20 years at 120° C.

After the pre-treatment is completed, an operator may perform validation tests on the pre-treated seal(s) 502. The validation tests may be performed while the pre-treated seal(s) 502 are exposed to a different fluid (e.g., nitrogen gas) rather than the previously used pre-treatment fluid. In other embodiments, the validation tests may be performed while the pre-treated seal(s) 502 are exposed to the previously used pre-treatment fluid.

Figure 6:
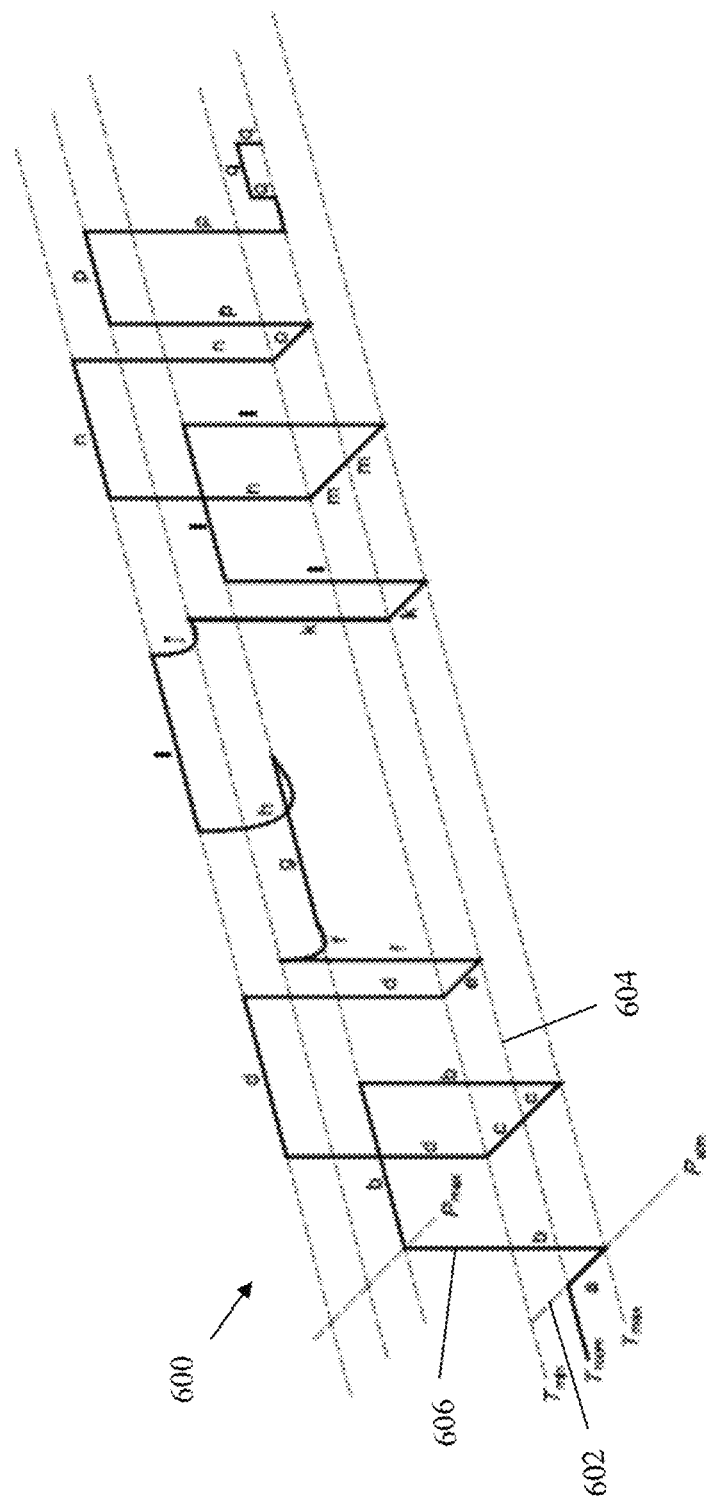
FIG. 6 is a three-dimensional representation of a validation procedure to be performed on a pre-treated seal, in accordance with an embodiment of the present disclosure.

FIG. 6 illustrates an example of a seal testing protocol that may be used as a basis for the additional seal functional tests. The seal testing protocol is illustrated as a three-dimensional plot 600 showing a progression of testing sequences (each sequence labeled with its own letter a through q). The three-dimensional plot 600 maps temperature ranging from $T_{min}$ to $T_{max}$ along a first axis 602, time along a second axis 604, and pressure ranging from $P_{min}$ to $P_{max}$ along a third axis 606. The time and pressure are varied at various times to complete the numerous testing sequences a through q. The seal testing protocol illustrated in FIG. 6 may be adapted from an existing seal test protocol such as, for example, API Spec 6A: Specification for Wellhead and Christmas Tree Equipment, Section F.1.11 (pressure and temperature cycles).

It should be noted that FIG. 6 provides an example of just one type of functional test that may be performed on the pre-treated seal(s) 502, and different tests may be possible as well (e.g., derivative test 138 of FIG. 1). Upon completion of the functional tests, an operator may remove the seals 502 from the test fixture and visually observe the seals. In other embodiments, sensors may be attached to the seals themselves or placed in various parts of the test assembly 500 to provide real-time data regarding seal performance of the pre-treated seals 502 during the validation testing.

The results of the pre-treatment and validation testing at the end-of-life condition may be used to determine whether the tested material is acceptable for use in the particular application for which it was tested. Specifically, an operator may determine whether to use a new seal having at least partially the same material composition as the pre-treated and validated seal in equipment within a subsea or subterranean environment based on the results of the one or more validation tests performed on the pre-treated seal. Upon determining to use the new seal, the method disclosed herein may include positioning equipment with the new seal into a subsea or subterranean environment and operating the equipment in the subsea or subterranean environment.

Although the present disclosure and its advantages have been described in detail, it should be understood that various changes, substitutions and alterations can be made herein without departing from the spirit and scope of the disclosure as defined by the following claims.

What is claimed is:

1. A method, comprising:
    establishing an Arrhenius relationship between a material response of a material exposed to a test fluid and an aging temperature of the material, based at least in part on experimental results of testing a plurality of material samples made of the material;
    determining, based at least in part on the Arrhenius relationship, a pre-treatment time and a pre-treatment temperature that approximates a seal end-of-life condition;
    pre-treating a seal by exposing the seal to the test fluid at the determined pre-treatment temperature for the determined pre-treatment time, the seal having at least in part a same material composition as the plurality of material samples; and
    after pre-treating the seal, performing one or more validation tests on the pre-treated seal.

2. The method of claim 1, wherein determining the pre-treatment time and the pre-treatment temperature comprises:
    determining or estimating a thermal half-life of the material response based on the Arrhenius relationship; and
    solving the equation:

$$t_{PT} = t_{App} \times 2^{\left(\frac{T_{PT} - T_{App}}{h}\right)},$$

wherein:
    h is the thermal half-life;
    $t_{PT}$ is the pre-treatment time;
    $t_{App}$ is an estimated lifetime of the seal;
    $T_{App}$ is the pre-treatment temperature; and
    $T_{PT}$ is an application temperature at which the seal is expected to be exposed during an application.

3. The method of claim 2, wherein $t_{PT}$ is a predetermined amount of time available for pre-treating the seal.

4. The method of claim 2, wherein determining the thermal half-life comprises:
    setting a time $t_1$ equal to a predetermined $t_{PT}$ value or $t_{App}$ value;
    determining a temperature $T_1$ corresponding to $t_1$ according to the Arrhenius relationship;
    setting a time $t_2$ equal to $t_1/2$;
    determining a temperature $T_2$ corresponding to $t_2$ according to the Arrhenius relationship; and
    subtracting $T_2$ from $T_1$.

5. The method of claim 4, wherein the thermal half-life (h) is an effective thermal half-life, wherein determining the effective thermal half-life comprises:
    determining a first thermal half-life using a time $t_1$ equal to a predetermined $t_{PT}$ value;
    determining a second thermal half-life using a time $t_1$ equal to a $t_{App}$ value; and
    averaging the first thermal half-life and the second thermal half-life.

6. The method of claim 2, wherein the thermal half-life is estimated, and wherein $t_{PT}$ is determined based on the estimated thermal half-life.

7. The method of claim 6, wherein the thermal half-life is estimated to be a value between −5 and −15 wherein $T_1$ and $T_2$ are in Kelvin.

8. The method of claim 6, further comprising determining $t_{PT}$ based on the equation $h = T_1 - T_2$, where:

$T_1$ is a temperature corresponding to $t_{PT}$ according to the Arrhenius relationship; and
$T_2$ is a temperature corresponding to $t_{PT}/2$ according to the Arrhenius relationship.

9. The method of claim 1, further comprising:
    providing the plurality of material samples;
    exposing each of the material samples to one or more portions of the test fluid; and testing the plurality of material samples after the material samples are exposed to the test fluid, wherein the Arrhenius relationship is established based on the results of the testing.

10. The method of claim 9, wherein testing the plurality of material samples comprises:
    exposing a first group of material samples of the plurality of material samples to a first portion of the test fluid at a first temperature;
    exposing a second group of material samples of the plurality of material samples to a second portion of the test fluid at a second temperature; and
    testing the first group of material samples and the second group of material samples.

11. The method of claim 10, wherein:
    testing the first group of material samples comprises:
        removing different material samples of the first group of material samples from the test fluid at different times; and
        performing a mechanical test on each of the material samples of the first group of material samples upon removing the material sample from the test fluid; and
    testing the second group of material samples comprises:
        removing different material samples of the second group of material samples from the test fluid at different times; and
        performing a mechanical test on each of the material samples of the second group of material samples upon removing the material sample from the test fluid.

12. The method of claim 11, wherein establishing the Arrhenius relationship comprises:
    fitting a first curve to a mechanical response of the first group of material samples with respect to time that the material samples were aged in the test fluid;
    fitting a second curve to a mechanical response of the second group of material samples with respect to time that the material samples were aged in the test fluid;
    calculating a first time to failure of material samples aged at the first temperature based on the first curve;
    calculating a second time to failure of material samples aged at the second temperature based on the second curve; and
    establishing the Arrhenius relationship by fitting a linear curve to two points corresponding to $(\ln(TtF_1), 1/T_1)$ and $(\ln(TtF_2), 1/T_2)$, wherein
    $T_1$ is the first temperature;
    $T_2$ is the second temperature;
    $TtF_1$ is the first time to failure; and
    $TtF_2$ is the second time to failure.

13. The method of claim 9, wherein testing the plurality of material samples further comprises:
    exposing each of the material samples to the one or more portions of the test fluid at a temperature $T_1$;
    removing different material samples of the plurality of material samples from the test fluid at different times; and
    performing a mechanical test on each of the material samples upon removing the material sample from the test fluid.

14. The method of claim 13, wherein establishing the Arrhenius relationship comprises:
    fitting a curve to a mechanical response of the plurality of material samples with respect to time that the material samples were aged in the test fluid;
    calculating a first time to failure ($TtF_1$) of the material samples aged at the temperature $T_1$ based on the curve;
    estimating a thermal half-life of the material response;
    calculating a second time to failure ($TtF_2$) equal to $TtF_1$ minus the estimated thermal half-life; and
    establishing the Arrhenius relationship by fitting a linear curve to two points corresponding to $(\ln(TtF_1), 1/T_1)$ and $(\ln(TtF_2), 1/T_2)$, wherein $T_2=T_1/2$.

15. The method of claim 14, wherein the thermal half-life is estimated to be a value between −5 and −15 wherein $T_1$ and $T_2$ are in Kelvin.

16. The method of claim 1, wherein the test fluid has a composition expected to be encountered by a seal located in subsea or subterranean equipment during a subsea or subterranean application.

17. The method of claim 1, wherein the material of the material samples and the seal is nonmetallic.

18. The method of claim 1, further comprising:
    determining whether to use a new seal having a same material composition as the seal in equipment within a subsea or subterranean environment based on results of the one or more validation tests performed on the pre-treated seal; and
    upon determining to use the new seal, positioning the equipment with the new seal into the subsea or subterranean environment; and
    operating the equipment in the subsea or subterranean environment.

19. The method of claim 1, wherein the one or more validation tests comprise a testing standard wherein the pre-treated seal is cycled through exposure to various pressures and temperatures in a predetermined sequence.

20. The method of claim 1, wherein the one or more validation tests comprise exposing the pre-treated seal to a second test fluid and an elevated pressure.

* * * * *